United States Patent
Takekoshi (10) Patent No.: US 11,330,051 B2
(45) Date of Patent: May 10, 2022

(54) RADIATION IMAGING SYSTEM AND METHOD OF CONTROLLING RADIATION IMAGING SYSTEM

(71) Applicant: CANON KABUSHIKI KAISHA, Tokyo (JP)

(72) Inventor: Koji Takekoshi, Fujisawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 133 days.

(21) Appl. No.: 16/810,138

(22) Filed: Mar. 5, 2020

(65) Prior Publication Data

US 2020/0296159 A1 Sep. 17, 2020

(30) Foreign Application Priority Data

Mar. 12, 2019 (JP) .............................. JP2019-045137

(51) Int. Cl.
*H04L 67/125* (2022.01)
*H04L 43/0811* (2022.01)
(Continued)

(52) U.S. Cl.
CPC .......... *H04L 67/1095* (2013.01); *G06F 9/542* (2013.01); *H04L 43/0811* (2013.01); *H04L 67/125* (2013.01); *H04L 67/36* (2013.01)

(58) Field of Classification Search
CPC ............. H04L 67/1095; H04L 43/0811; H04L 67/125; H04L 67/36; G06F 9/542;
(Continued)

(56) References Cited

U.S. PATENT DOCUMENTS

2005/0046642 A1* 3/2005 Takekoshi ............ A61B 6/5241
345/619
2010/0111257 A1* 5/2010 Takekoshi ............ A61B 6/563
378/91

(Continued)

FOREIGN PATENT DOCUMENTS

JP 2014211764 A 11/2014
JP 6195348 B2 9/2017

OTHER PUBLICATIONS

U.S. Appl. No. 16/808,921, filed Mar. 4, 2020 to Hironori Yamashita and entitled "Radiation Imaging System and Method of Controlling Radiation Imaging System".

(Continued)

*Primary Examiner* — Shirley X Zhang
(74) *Attorney, Agent, or Firm* — Carter, DeLuca & Farrell LLP (57) ABSTRACT

A radiation imaging system that can control a radiation generating apparatus and a radiation detector based on communication between a first control application and a second control application, the system comprises: a connection monitoring unit configured to monitor a connection state of the communication; a holding unit configured to hold an information notification indicating a control state of an imaging control unit of the first control application that performs the control in a case where the connection monitoring unit determines that the connection state is a disconnection state; and a deletion processing unit configured to perform deletion processing of an information notification held in the holding unit so as to leave an information notification indicating a final state of control by the imaging control unit.

17 Claims, 8 Drawing Sheets

(51) Int. Cl.
  *G06F 9/54* (2006.01)
  *G16H 40/67* (2018.01)
  *A61B 6/00* (2006.01)
  *H04L 67/1095* (2022.01)
  *H04L 67/75* (2022.01)

(58) Field of Classification Search
  CPC ........ G16H 40/63; G16H 30/20; G16H 40/67; A61B 6/464; A61B 6/54; A61B 6/56; A61B 6/00; A61B 6/42; A61B 6/40
  See application file for complete search history.

(56) References Cited

U.S. PATENT DOCUMENTS

| | | | |
|---|---|---|---|
| 2011/0026676 A1* | 2/2011 | Takekoshi | A61B 6/58 378/98.2 |
| 2012/0288064 A1* | 11/2012 | Takekoshi | A61B 6/58 378/98.2 |
| 2016/0364484 A1* | 12/2016 | Dong | H04L 67/28 |
| 2017/0251989 A1 | 9/2017 | Nishii | |
| 2018/0368797 A1 | 12/2018 | Kuwata et al. | |
| 2019/0098074 A1* | 3/2019 | He | H04L 67/10 |
| 2019/0231297 A1* | 8/2019 | Takekoshi | G16H 40/60 |
| 2020/0296159 A1* | 9/2020 | Takekoshi | H04L 67/125 |

OTHER PUBLICATIONS

Extended European Search Report issued by the European Patent Office dated Jul. 13, 2020 in corresponding EP Patent Application No. 20159700.2.

Extended European Search Report issued by the European Patent Office dated Aug. 7, 2020 in corresponding EP Application No. 20160033.5-112.

* cited by examiner

RADIATION IMAGING SYSTEM AND METHOD OF CONTROLLING RADIATION IMAGING SYSTEM

BACKGROUND OF THE INVENTION

Field of the Invention

The present invention relates to a radiation imaging system and a method of controlling the radiation imaging system and, more particularly, to a technique for causing an application for controlling radiation imaging and another application to operate in cooperation with each other.

Description of the Related Art

In recent years, the digitization of radiation imaging systems has led to the proliferation of systems designed to irradiate a radiation imaging apparatus with radiation from a radiation source through an object, make the radiation imaging apparatus generate a digital radiation image, and enable checking of the image immediately after imaging. In addition, advances in network link technology have enabled pieces of software in different apparatuses to operate in cooperation with each other.

Japanese Patent No. 6195348 discloses an invention designed to prevent collision between operations, by using a known remote desktop mechanism called Splashtop Touchpad, when a plurality of user terminals are simultaneously operated in a medical system and a medical apparatus including one operation terminal and a plurality of user terminals that operate while communicating with each other. According to the invention disclosed in Japanese Patent No. 6195348, priorities are assigned to operations depending on operators, operating places, and the roles of operators.

The medical system disclosed in Japanese Patent No. 6195348 is based on the premise of using remote desktops, and cannot enable cooperation of processes between applications having different GUIs, processes between applications operating on different OSs (Operating Systems), that is, processes between a plurality of applications.

Assume that in a system in which a plurality of applications cooperate to execute processing, applications are disconnected from each other. In this case, in order to resume a cooperative operation, it is necessary to solve an information mismatch caused between the two applications after the restoration of connection.

The present invention provides a technique capable of solving an information mismatch caused between applications by performing deletion processing of held information notifications so as to leave an information notification representing the final state of control, in a system having a plurality of applications designed to execute processing in cooperation with each other, even when the applications are disconnected from each other and then reconnected again.

SUMMARY OF THE INVENTION

According to one aspect of the present invention, there is provided a radiation imaging system that can control a radiation generating apparatus and a radiation detector based on communication between a first control application and a second control application, the system comprising: a connection monitoring unit configured to monitor a connection state of the communication; a holding unit configured to hold an information notification indicating a control state of an imaging control unit of the first control application that performs the control in a case where the connection monitoring unit determines that the connection state is a disconnection state; and a deletion processing unit configured to perform deletion processing of an information notification held in the holding unit so as to leave an information notification indicating a final state of control by the imaging control unit.

According to another aspect of the present invention, there is provided a method of controlling a radiation imaging system that can control a radiation generating apparatus and a radiation detector based on communication between a first control application and a second control application, the method comprising: monitoring a connection state of the communication; holding an information notification indicating a control state of an imaging control unit of the first control application that performs the control in a case where it is determined in the monitoring that the connection state is a disconnection state; and performing deletion processing of an information notification held in the holding unit so as to leave an information notification indicating a final state of control by the imaging control unit.

The present invention can solve an information mismatch caused between applications by performing deletion processing of held information notifications so as to leave an information notification representing the final state of control.

Further features of the present invention will become apparent from the following description of exemplary embodiments (with reference to the attached drawings).

DESCRIPTION OF THE EMBODIMENTS

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

First Embodiment (Example of Arrangement of Radiation Imaging System)

Figure 1:
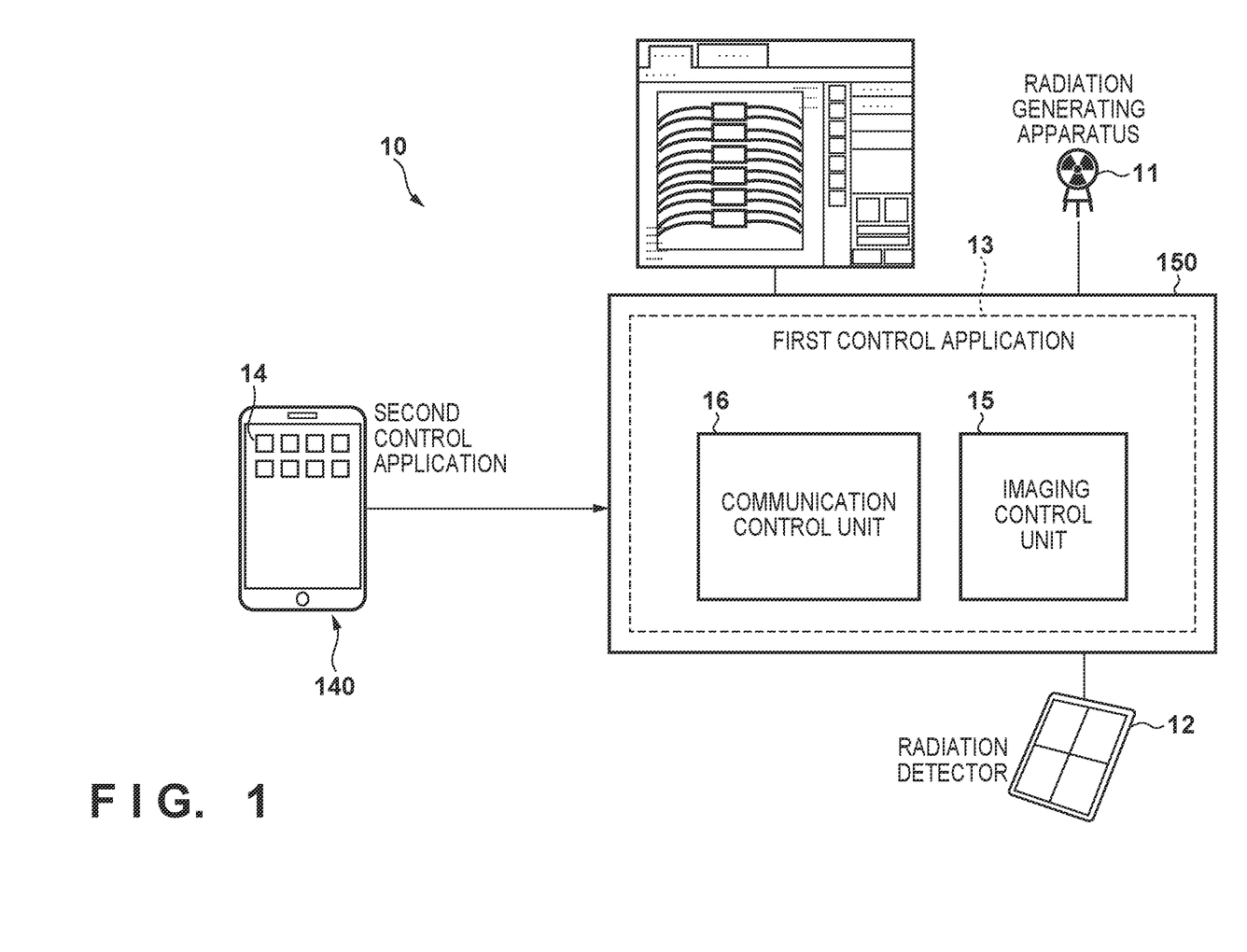
FIG. 1 is a view showing an example of the arrangement of a radiation imaging system according to the first embodiment.

FIG. 1 shows an example of the arrangement of a radiation imaging system 10 according to the first embodiment. In many hospitals, mainly a radiation imaging technician (to be also referred to as an operator hereinafter) operates an imaging control apparatus 150 while viewing the display device (monitor) on a console to make the imaging control apparatus 150 control a radiation generating apparatus 11 and a radiation detector 12, thus obtaining a radiation image.

A first control application 13 is, for example, an application operating in the imaging control apparatus 150. The first control application 13 performs display control to provide a GUI (graphical user interface) for the display device (monitor). The GUI displays information for assisting the operator to control the radiation imaging system for radiation imaging and information for assisting imaging, such as subject information.

For example, the radiation imaging system 10 is configured to allow the first control application 13 to operate in cooperation with a second control application 14 in another terminal (for example, a portable terminal 140).

The second control application 14 is an application that can operate in the portable terminal 140 and other types of information devices and performs display control to provide the display unit of the portable terminal 140 with a GUI for presenting information to the operator. Information different from or identical to the contents displayed on the GUI provided by display control of the first control application 13 may be displayed/notified to the GUI of the portable terminal 140. Note that this system may include a plurality of portable terminals and can also use a wearable terminal as long as it can achieve the object of providing information to the operator.

(Procedure for Examination)

A general procedure for an examination will be described next. First of all, the operator receives an order for radiation imaging via an in-hospital network. The imaging order is received in the imaging control apparatus 150 and specifies subject information and the contents of imaging. In general, when an imaging order is delivered to the operator, a subject waits for imaging outside an examination room. The operator calls the subject into the examination room and prepares for an examination in accordance with the imaging order. Upon calling the subject into the examination room, the operator checks the name and birth date of the subject to prevent a mix-up between subjects. At this time, for example, the operator makes a check by matching the subject name on the imaging order received as subject information with the information displayed on the screen of the portable terminal 140.

Upon completing preparation for imaging, the operator adjusts the positions of the radiation generating apparatus 11, the subject, and the radiation detector 12. The operator can change, for example, the order of imaging and the position of the subject at the time of imaging between, for example, a standing position and a supine position at the discretion of the operator depending on the state of the subject or the contents of the imaging order.

Subsequently, upon determining that radiation imaging can be performed, the operator inputs an instruction to start imaging to an operation unit (not shown). The imaging control apparatus 150 controls the radiation generating apparatus 11 and the radiation detector 12 based on the operation of the operation unit to cause the radiation generating apparatus 11 to apply radiation and the radiation detector 12 to detect radiation transmitted through a subject. The radiation detector 12 includes a pixel array in which a plurality of pixels for converting radiation into electrical signals are arranged in a matrix pattern, and can generate a radiation image corresponding to the converted electrical signals.

The imaging control apparatus 150 is configured to be communicable with the radiation detector 12, and obtains the radiation image generated by the radiation detector 12 by communication. The imaging control apparatus 150 performs display control to display the obtained radiation image on the display device (monitor). Upon checking the radiation image displayed on the monitor and finding no problem, the operator moves to the examination room to set a next imaging position, and performs imaging in the same procedure. If there is no need to perform next imaging, the examination is terminated, and the subject leaves the imaging room.

(Functional Arrangement of Radiation Imaging System)

Figure 2:
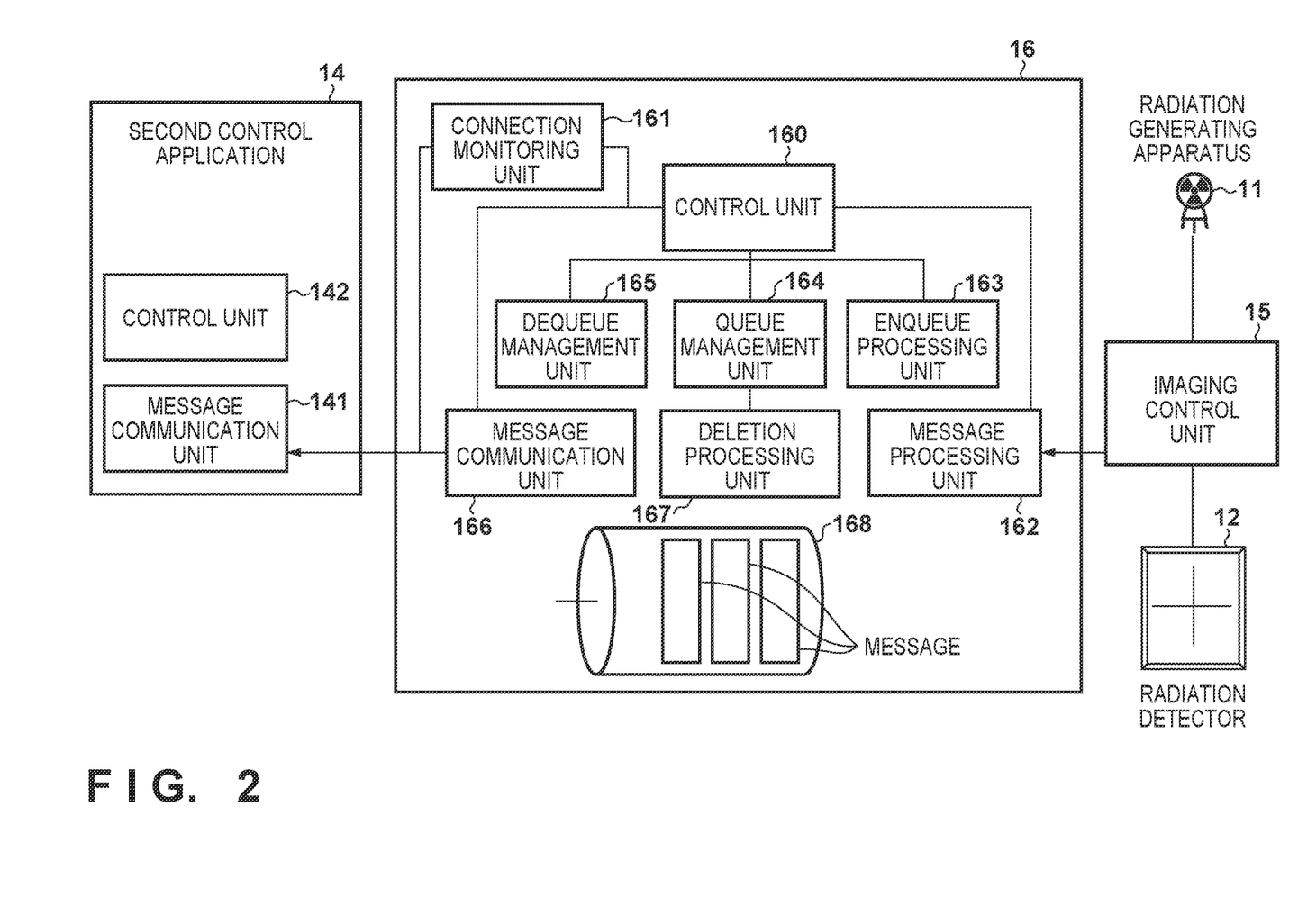
FIG. 2 is a block diagram exemplarily showing the functional arrangement of the radiation imaging system.

The functional arrangement of the radiation imaging system will be described next with reference to FIG. 2. The radiation imaging system 10 includes the radiation generating apparatus 11 that generates radiation, the radiation detector 12 that detects radiation, and the imaging control apparatus 150 (computer) that controls the radiation generating apparatus 11 and the radiation detector 12. The radiation imaging system 10 can control the radiation generating apparatus 11 and the radiation detector 12 based on communication between the first control application and the second control application. The first control application 13 is, for example, an application operating on the imaging control apparatus 150 (computer). Processing by each unit constituting the first control application 13 is implemented as a functional component of the imaging control apparatus 150.

The second control application 14 may be an application operating on the same computer on which the first control application 13 operates or an application operating on a computer (for example, the portable terminal 140) different from the imaging control apparatus 150 (computer) on which the first control application 13 operates. In addition, the second control application 14 need not be a single application and may include a plurality of applications providing different GUIs.

The functional arrangement of the first control application 13 will be described next. The first control application 13 is constituted by an imaging control unit 15 and a communication control unit 16. The imaging control unit 15 is the main logic unit of the first control application 13 which provides a GUI, controls display on the GUI, and executes imaging control in the radiation imaging system 10. The imaging control unit 15 can operate singly and controls the radiation imaging system 10 while making the radiation generating apparatus 11 and the radiation detector 12 cooperate with each other.

The communication control unit 16 is a DLL (Dynamic Link Library) that operates as a plugin of the imaging control unit 15. A plugin structure allows the imaging control unit 15 and the communication control unit 16 to operate in cooperation with each other as well as allowing the imaging control unit 15 to operate singly. The DLL need not always have a plugin structure, and the imaging control unit 15 and the communication control unit 16 may be configured to operate in cooperation with each other. This embodiment will be described on the premise that the DLL has a plugin structure.

The internal operation of the communication control unit 16 will be described next. A control unit 160 as a functional component of the communication control unit 16 controls the overall internal operation of the communication control unit 16. A message processing unit 162 performs reception processing of information from the imaging control unit 15 of the first control application 13. When information to be notified to the second control application 14 in accordance with the operation of the imaging control unit 15 is generated, the imaging control unit 15 notifies the communication control unit 16 of the information. In this case, information received from the imaging control unit 15 of the first control application 13 will be referred to as an information notification or message. In this case, information notifications include a notification concerning a screen transition of the GUI provided by the first control application 13 and a notification concerning the in-screen operation of the GUI. In addition, information notifications include a notification concerning the state of radiation imaging by the imaging control unit 15 of the first control application 13.

An enqueue processing unit 163 holds (enqueues) the message received by the message processing unit 162 in a processing waiting queue 168 under the control of the control unit 160. Upon enqueuing the message, the control unit 160 controls a queue management unit 164 and a deletion processing unit 167 to manage the messages queued in the processing waiting queue 168.

A dequeue management unit 165 (obtaining unit) obtains (dequeues) a message held in the processing waiting queue 168 under the control of the control unit 160. The dequeue management unit 165 obtains a message from the processing waiting queue 168 according to the FIFO (First In First Out) principle. A message communication unit 166 transmits the message obtained by the dequeue management unit 165 (obtaining unit) to a message communication unit 141 of the second control application 14.

The communication control unit 16 is connected to the second control application 14 via a wired or wireless network. A connection monitoring unit 161 that monitors the connection state of communication monitors the connection state of the network or the connection state originating from the operation state between applications. The control unit 160 controls the obtaining of an information notification (message) held in the processing waiting queue 168 (holding unit) based on the monitoring result obtained by the connection monitoring unit 161.

If the connection monitoring unit 161 determines a disconnection state, the control unit 160 causes the dequeue management unit 165 (obtaining unit) to stop obtaining an information notification (message). Upon determining a state in which it is not possible to communicate with the second control application 14, that is, a disconnection state, the connection monitoring unit 161 notifies the queue management unit 164 via the control unit 160 that no message queued in the processing waiting queue 168 can be processed. Upon being notified that no message can be processed, the queue management unit 164 stops dequeue processing by the dequeue management unit 165. If the connection monitoring unit 161 determines that the connection state is a disconnection state, the processing waiting queue 168 sequentially holds an information notification (message) indicating the control state of the imaging control unit 15 of the first control application 13.

In contrast, if the connection monitoring unit 161 determines a reconnection state after determining a disconnection state, the control unit 160 causes the dequeue management unit 165 (obtaining unit) to resume obtaining an information notification (message). That is, upon detecting a reconnection state while dequeue processing is stopped, the connection monitoring unit 161 notifies the queue management unit 164 via the control unit 160 that queue processing can be performed. Upon being notified that queue processing can be performed, the queue management unit 164 resumes dequeue processing by the dequeue management unit 165.

If the connection monitoring unit 161 determines a reconnection state after determining a disconnection state, the control unit 160 causes the dequeue management unit 165 (obtaining unit) to resume obtaining an information notification (message). The message communication unit 166 then obtains an information notification from the processing waiting queue 168 having undergone deletion processing by the deletion processing unit 167, and transmits the notification to the message communication unit 141 of the second control application 14.

(Procedure of Processing in Communication Control Unit 16)

A procedure of processing in the communication control unit 16 will be described with reference to the flowchart of FIG. 7 and FIGS. 3 to 6. The deletion processing unit 167 of the communication control unit 16 executes the processing shown in FIG. 7. The deletion processing unit 167 performs deletion processing of a plurality of information notifications (messages) held in the processing waiting queue 168 by performing deletion processing based on the attributes of the information notifications (messages). That is, the deletion processing unit 167 performs deletion processing of the information notifications (messages) held in the processing waiting queue 168 so as to leave an information notification (message) representing the final state of control by the imaging control unit 15 of the first control application 13.

Figure 7:
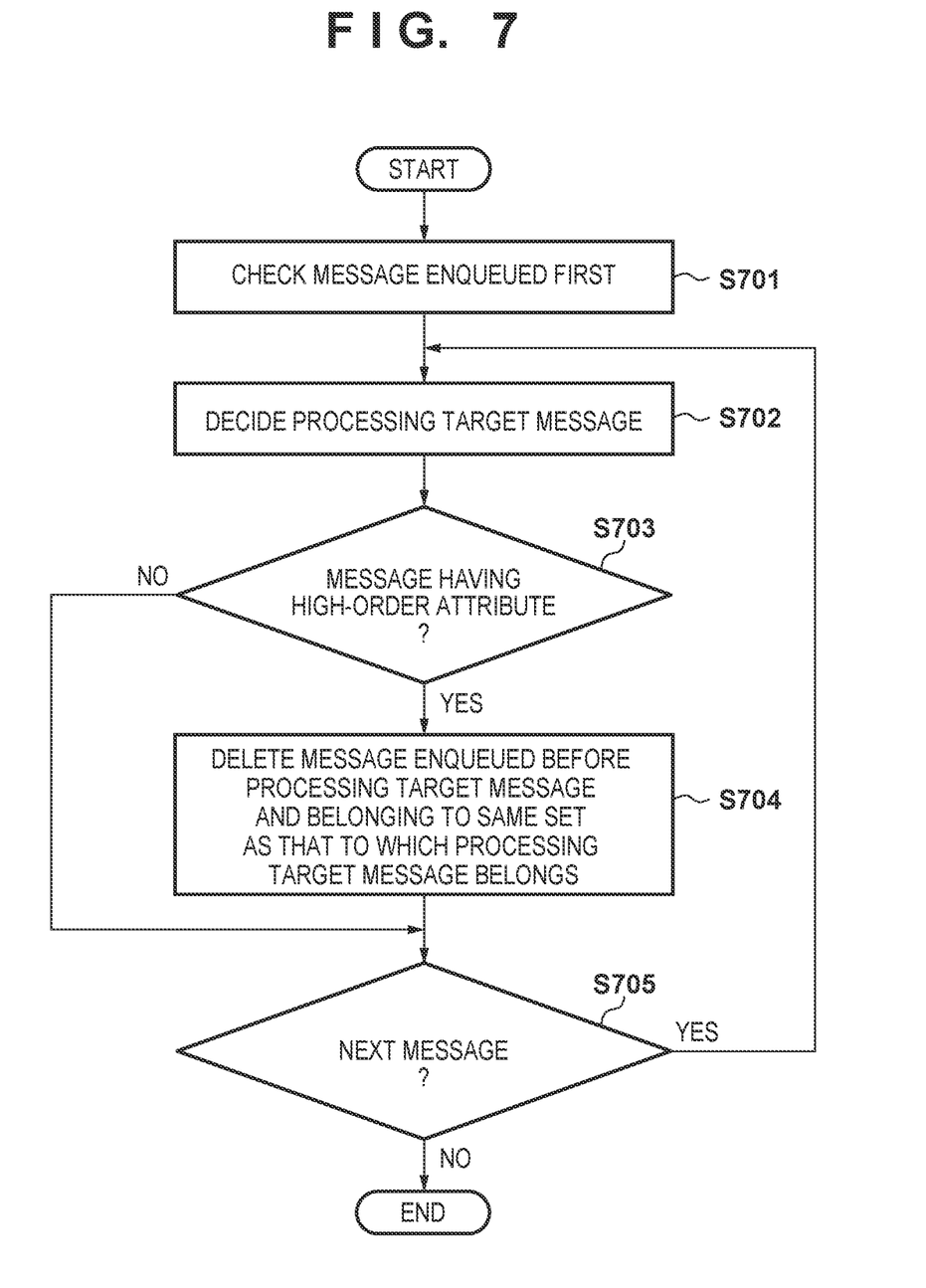
FIG. 7 is a flowchart for explaining processing in a communication control unit according to the first embodiment.

Assume as preconditions that the connection monitoring unit 161 has determined a disconnection state, and dequeue processing by the dequeue management unit 165 has stopped. Assume that in this case, the determination of a disconnection state includes the determination of a connection/non-connection state of a network itself and the determination of a connection/non-connection state depending on the activation state of an application.

Figure 3:
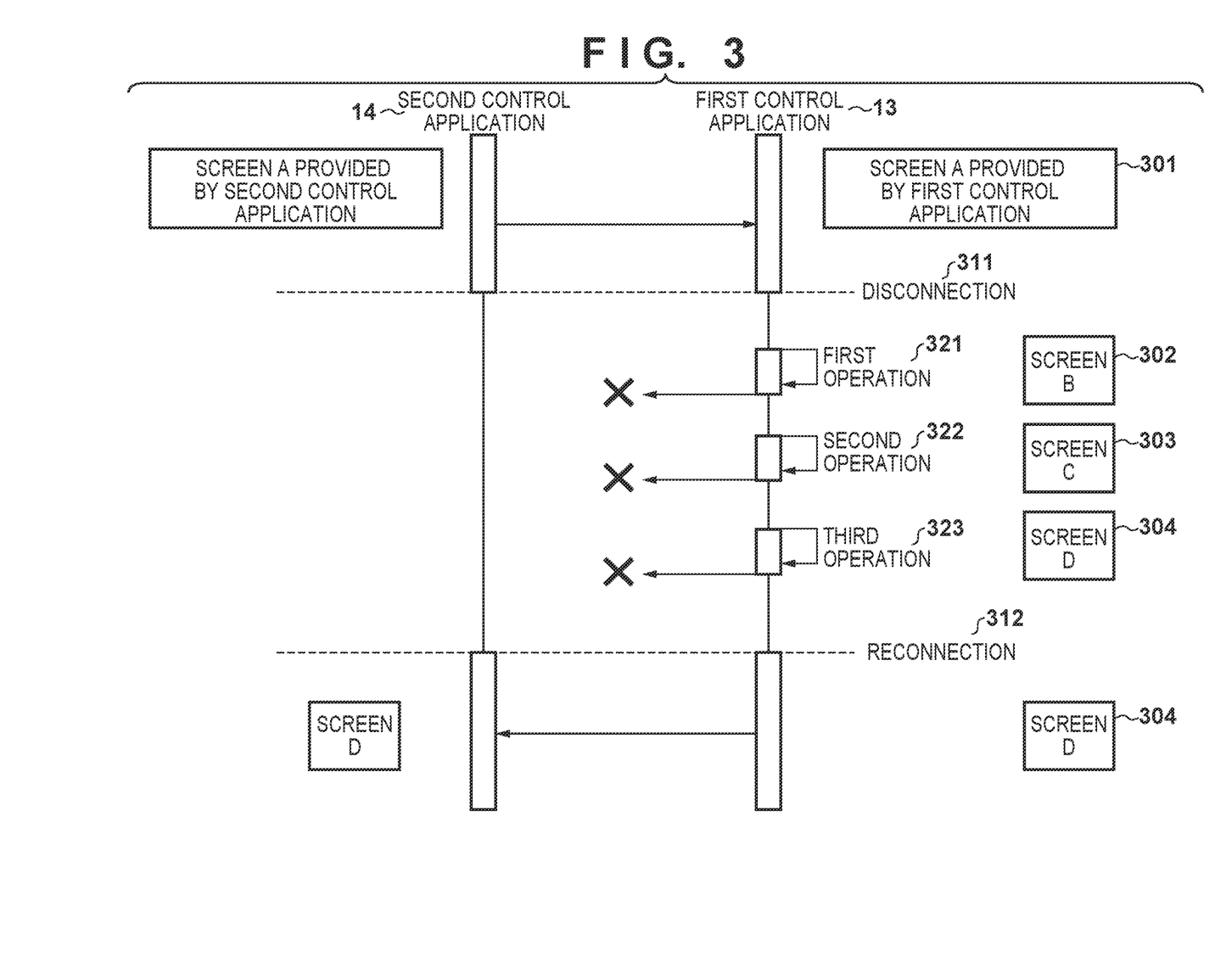
FIG. 3 is a view showing an example of the occurrence of an information mismatch caused by communication disconnection.

FIG. 3 shows a case in which when the communication state between the first and second control applications becomes a non-connection state, an information mismatch occurs between the first and second control applications. For example, as shown in the sequence chart of FIG. 3, assume that a disconnection 311 has occurred because of a network disconnection, an application trouble on the second control application 14 side, or the like in a state in which the first control application 13 and the second control application 14 are in a connection state (a state in which screen A is displaying an operation screen in a display state 301). In this state, when the first control application 13 executes a first operation 321 on screen B in a display state 302, a second operation 322 on screen C in a display state 303, and a third operation 323 on screen D in a display state 304, the first control application 13 can transmit no information concerning each operation to the second control application 14 because of the disconnection state.

When no message can be transmitted between the first and second control applications, the connection monitoring unit 161 determines a disconnection state and notifies the queue management unit 164 via the control unit 160 that no message queued in the processing waiting queue 168 can be processed. Based on this notification, the queue management unit 164 stops dequeue processing by the dequeue management unit 165. The dequeue management unit 165 stops operating the dequeue management unit to stop message communication. Note that because it is important to transmit no message, a connection state may be monitored by detecting an error upon transmitting a message in consideration of software design and implementation. Likewise, dequeuing may be stopped because of a message transmission error.

When the imaging control unit 15 operates to generate an information notification while no message can be transmitted, messages to be transmitted to the second control application 14 are sequentially held and retained in the processing waiting queue 168.

That is, because no messages concerning the first operation 321 on screen B, the second operation 322 on screen C, and the third operation 323 on screen D can be transmitted, GUI screen A provided by the second control application 14 is not updated. This causes a mismatch with the display state 304 on screen D on the GUI provided by the first control application 13. That is, when a connection state changes to a disconnection state, an information mismatch occurs between the first and second control applications.

In this embodiment, in order to prevent the occurrence of an information mismatch between the first and second control applications, the deletion processing unit 167 performs deletion processing of the messages held in the processing waiting queue 168 so as to delete the messages, of the plurality of messages held in the processing waiting queue 168, which concern the first operation 321 on screen B and the second operation 322 on screen C shown in FIG. 3 and leave only the message concerning the third operation 323 on screen D.

The deletion processing unit 167 performs deletion processing of information notifications (messages) held in the processing waiting queue 168 so as to leave an information notification representing the final state of control by the imaging control unit 15.

Leaving only the message concerning the third operation 323 on screen D in the processing waiting queue 168 will transmit the message concerning the third operation 323 on screen D left in the processing waiting queue 168 to the second control application 14 when the communication state between the first and second control applications becomes a connection state (reconnection 312). The display state 304 of screen D on the newest (latest) GUI provided by the first control application 13 matches GUI screen D provided by the second control application 14 to solve the information mismatch between the first and second control applications.

More specifically, the communication control unit 16 executes the following processing procedure while messages are retained. In this processing procedure, for example, while the dequeue management unit 165 of the communication control unit 16 stops dequeue processing, the deletion processing unit 167 of the communication control unit 16 executes processing at the occurrence of a next queue (first queue), in response to a start notification by a timer, or the like.

In step S701 in FIG. 7, the deletion processing unit 167 checks one of the messages held in the processing waiting queue 168 (queue holding unit) which is held (enqueued) in the processing waiting queue 168 first after the stoppage of dequeue processing.

In step S702, the deletion processing unit 167 decides a processing target message. In this embodiment, messages are sequentially processed, starting from the message held (enqueued) first in the processing waiting queue 168 after the stoppage of dequeue processing. The first processing target is the oldest one of the messages held in the processing waiting queue 168, and newer messages are sequentially set as processing targets afterward.

In step S703, the deletion processing unit 167 determines whether a processing target message is a message having a high-order attribute. In this case, a high-order attribute corresponds to a message as a parent of a message subset constituted by a plurality of messages. A message subset includes a message as a parent (main message) and associated messages associated with the main message. For example, in the case shown in FIG. 6, in a message subset 61*a*, the main message as the parent is a screen A 611. In a message subset 62*b*, the main message as the parent is a screen B 621.

That is, in the processing in step S703, the deletion processing unit 167 determines whether the processing target message is the parent (main message) of the subset. For example, as shown in FIG. 3, when a screen transition has occurred from the display state 301 on screen A to the display state 302 on screen B on the GUI provided by the imaging control unit 15, the imaging control unit 15 notifies the message processing unit 162 of the communication control unit 16 of a message indicating a screen transition to screen B (for example, the message indicating the screen B 621 in FIG. 6). This message becomes a main message having a high-order attribute. If the deletion processing unit 167 determines in step S703 that the processing target message is not a message having a high-order attribute (main message) (NO in step S703), the process advances to step S705, in which the deletion processing unit 167 determines whether there is any next message held in the processing waiting queue 168.

If the deletion processing unit 167 determines in step S705 that there is a next message (YES in step S705), the process returns to step S702 to repeat similar processing. If the deletion processing unit 167 determines in step S705 that the processing waiting queue 168 holds no next message (NO in step S705), this processing is terminated.

Upon determining in step S703 that the processing target message is a message having a high-order attribute (main message) (YES in step S703), the deletion processing unit 167 advances the process to step S704.

In step S704, the deletion processing unit 167 specifies messages belonging to the same subset as that to which the message (main message) belongs from the messages held (enqueued) in the processing waiting queue 168 before the message currently set as a processing target, and deletes all the specified messages. For example, in the case shown in FIG. 6, if the screen A 611 as a message having a high-order attribute (main message) is a processing target message, messages (associated messages) concerning operations 612 to 615 belonging to the same subset 61*a* as that to which the screen A 611 belongs become deletion targets.

That is, if the processing target information notification (message) held first in the processing waiting queue 168 after determination of a disconnection state is an information notification having a high-order attribute (main message), the deletion processing unit 167 specifies an information notification subset constituted by the information notification having the high-order attribute (main message) and information notifications (associated messages) associated with the information notification having the high-order attribute. The deletion processing unit 167 then performs deletion processing of the information notifications belonging to the subset of information notifications held (enqueued) in the processing waiting queue 168 before the processing target information notification.

(Specific Example of Processing)

Figure 4:
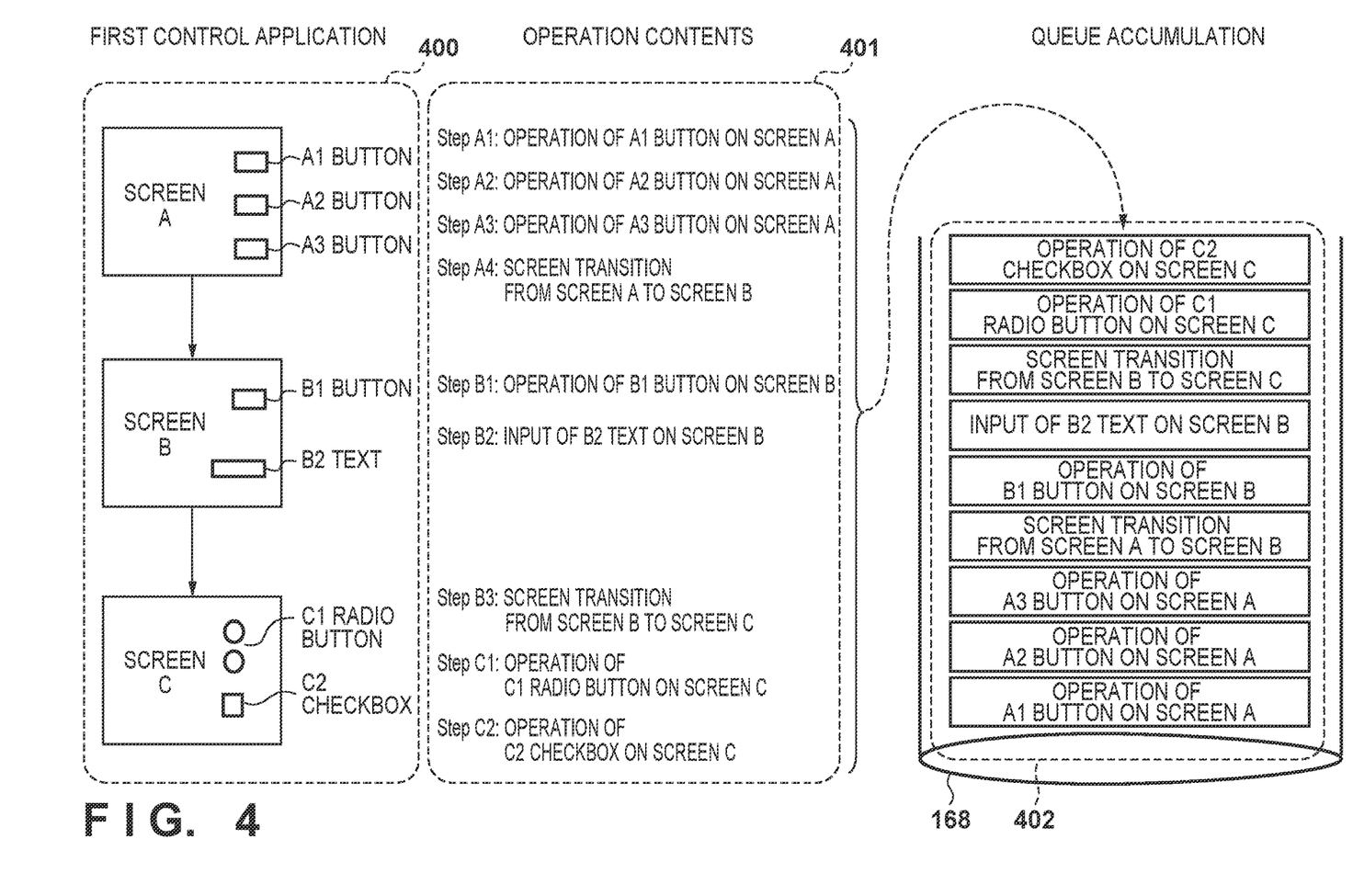
FIG. 4 is a view showing a specific example of processing according to the first embodiment.

FIG. 4 shows a specific example of processing. A GUI screen 400 in FIG. 4 indicates a GUI screen transition provided by display control of the imaging control unit 15 in the first control application 13. An operation 401 indicates an operation procedure with respect to the GUI screen. Assume that when the operation 401 is executed, the first and second control applications are in a non-connection state.

In the operation 401, Step A1 to Step A3 respectively indicate A1 button to A3 button on screen A. Step A4 is the screen transition operation of switching from screen A to screen B. Step B1 and Step B2 respectively indicate a B1 button operation and a B2 text input operation on screen B. Step B3 is a screen transition operation of switching from screen B to screen C. Step C1 and Step C2 respectively indicate a C1 radio button operation and C2 checkbox operation on screen C.

Assume that the operation 401 is performed, and messages are held in the processing waiting queue 168 without performing deletion processing of messages. In this case, messages 402 are sequentially held in the processing waiting queue 168.

For example, in step S705 in FIG. 7, the message held (enqueued) first in the processing waiting queue 168 is processed as a processing target, and subsequent messages are sequentially processed. If there is a message next to the message currently processed as a processing target, subsequent processing is executed for the processing target message in step S702. If there is no next message, the processing is terminated.

Figure 6:
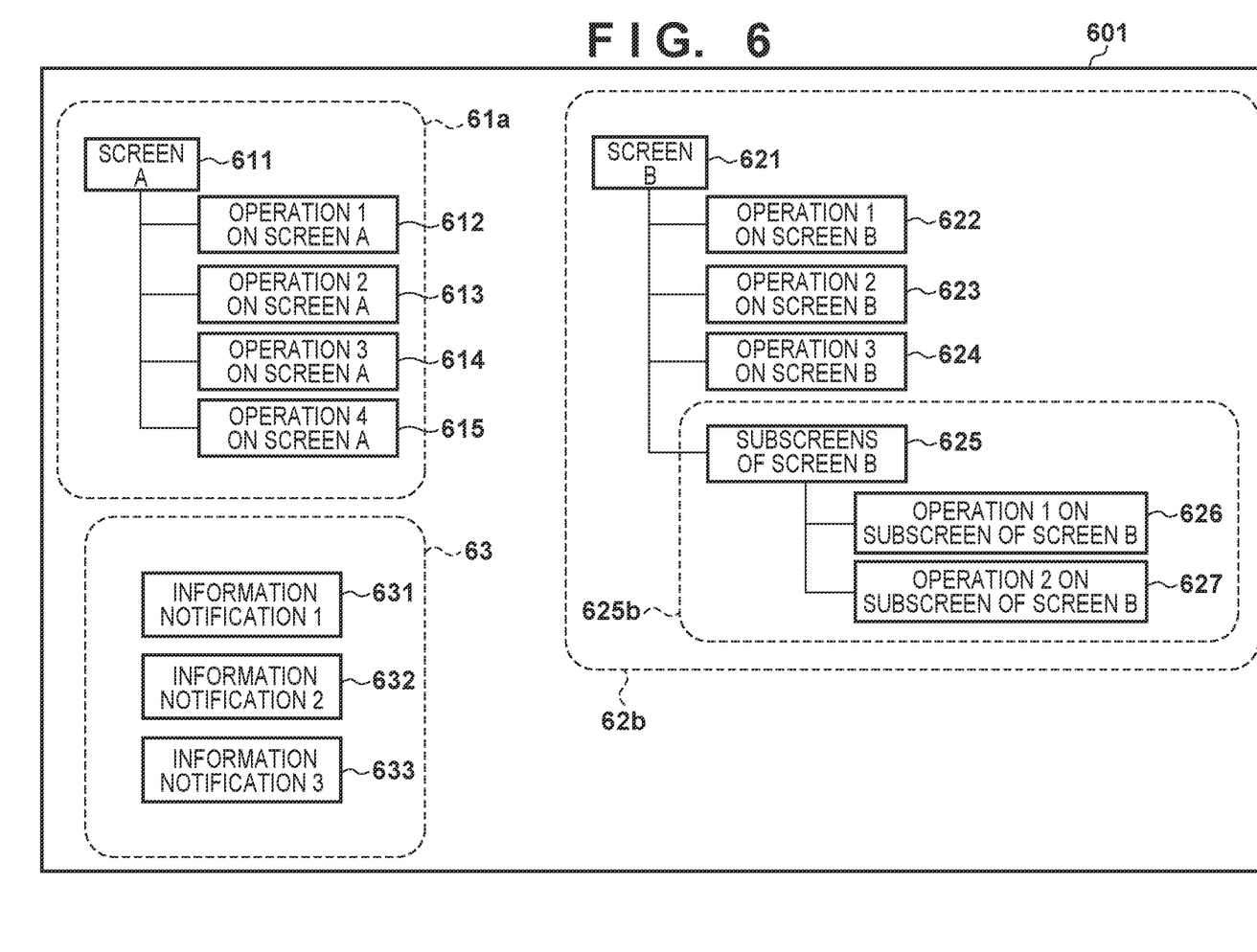
FIG. 6 is a block diagram exemplarily showing a message set constituted by a plurality of messages.

FIG. 6 exemplarily shows a message set constituted by a plurality of messages. In the subset 61a, the message having the high-order attribute indicates a screen transition to the screen A 611 (FIG. 4). In the set 62b, the message having the high-order attribute indicates a screen transition to the screen B 621 (FIG. 4). Assume that the operation 401 in FIG. 4 is performed under the control of the imaging control unit 15. The message 402 notified in this case is held in the processing waiting queue 168.

Figure 5:
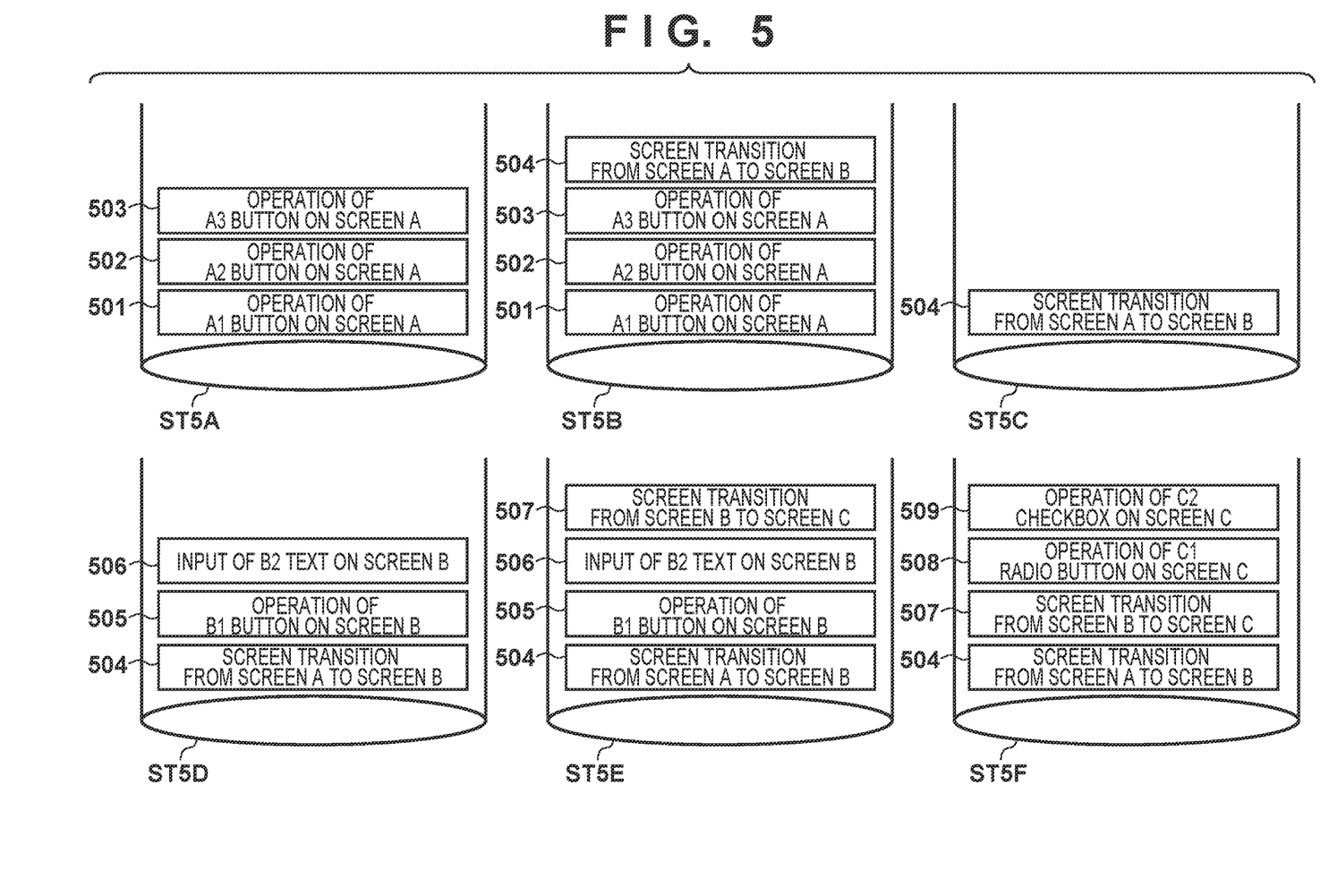
FIG. 5 is a block diagram exemplarily showing messages sequentially held in a processing waiting queue.

FIG. 5 exemplarily shows messages to be sequentially held in the processing waiting queue 168. If the operations 401 in FIG. 4 are sequentially performed, messages corresponding to the operations 501 to 503 (Step A1 to Step A3 in FIG. 4) in screen A are sequentially held (enqueued) in the processing waiting queue 168 (ST5A). Although the processing in each step in the flowchart of FIG. 7 is also performed during this period, because any message is not determined as a message having a high-order attribute (main message) in step S703, target messages are sequentially held in the processing waiting queue 168. Subsequently, when a message 504 indicating a screen transition from screen A to screen B (Step A4 in FIG. 4) is held (enqueued) in the processing waiting queue 168, the holding state of the processing waiting queue 168 becomes the state indicated by ST5B. In this case, the message indicating the screen transition from screen A to screen B is the message having the high-order attribute (main message) in the subset 61a, and hence deletion processing in step S704 is performed in the processing shown in FIG. 7. In this case, the deletion processing unit 167 specifies messages (associated messages (501 to 503)) belonging to the same subset 61a as that to which the message 504 (main message) belongs from the messages (501 to 503) held (enqueued) in the processing waiting queue 168, and deletes all the specified messages (associated messages (501 to 503)). The result obtained by executing the deletion processing becomes the state indicated by ST5C.

Likewise, messages corresponding to operations 505 and 506 (Step B1 and Step B2 in FIG. 4) in screen B are sequentially held (enqueued) in the processing waiting queue 168 (ST5D). Although the processing in each step in the flowchart of FIG. 7 is also performed during this period, because any message is not determined as a message having a high-order attribute (main message) in step S703, target messages are sequentially held in the processing waiting queue 168. Subsequently, when a message 507 indicating a screen transition from screen B to screen C (Step B3 in FIG. 4) is held (enqueued) in the processing waiting queue 168, the holding state of the processing waiting queue 168 becomes the state indicated by ST5E. In this case, the message indicating the screen transition from screen B to screen C is the message 507 having the high-order attribute (main message) in the subset 62b, and hence deletion processing in step S704 is performed in the processing shown in FIG. 7. In this case, the deletion processing unit 167 specifies messages (associated messages (505 and 506)) belonging to the same subset 62b as that to which the message 507 (main message) belongs from the messages (504 to 506) held (enqueued) in the processing waiting queue 168 before the message 507 as a current processing target, and deletes all the specified messages (associated messages (505 and 506)).

Messages corresponding to operations 508 and 509 (Step C1 and Step C2 in FIG. 4) in screen C are sequentially held (enqueued) in the processing waiting queue 168 (ST5F). Although the processing in each step in the flowchart of FIG. 7 is also performed during this period, because any message is not determined as a message having a high-order attribute (main message) in step S703, target messages are sequentially held in the processing waiting queue 168. This result becomes the state indicted by ST5F. The messages corresponding to in-screen operations on screen A and screen B are deleted, and only the message corresponding to the screen transition is left in the processing waiting queue 168. In addition, the messages 5084 and 509 corresponding to screen operations on final screen C are left in the processing waiting queue 168. With this operation, the message indicating the final state is held in the processing waiting queue 168. When connection is resumed between the first and second control applications, the message held in the processing waiting queue 168 and indicating the final state of control becomes a message as a transmission target to be transmitted to the second control application. Although this embodiment has exemplified a screen transition, a message set or subset is not limited to screen transitions or in-screen operations, and may be classifications having some kinds of meanings. For example, messages corresponding to operations between the start of an examination and the end of the examination may be grouped into a subset or messages corresponding to operations for one unit of imaging may be grouped into a subset.

Second Embodiment

Figure 8:
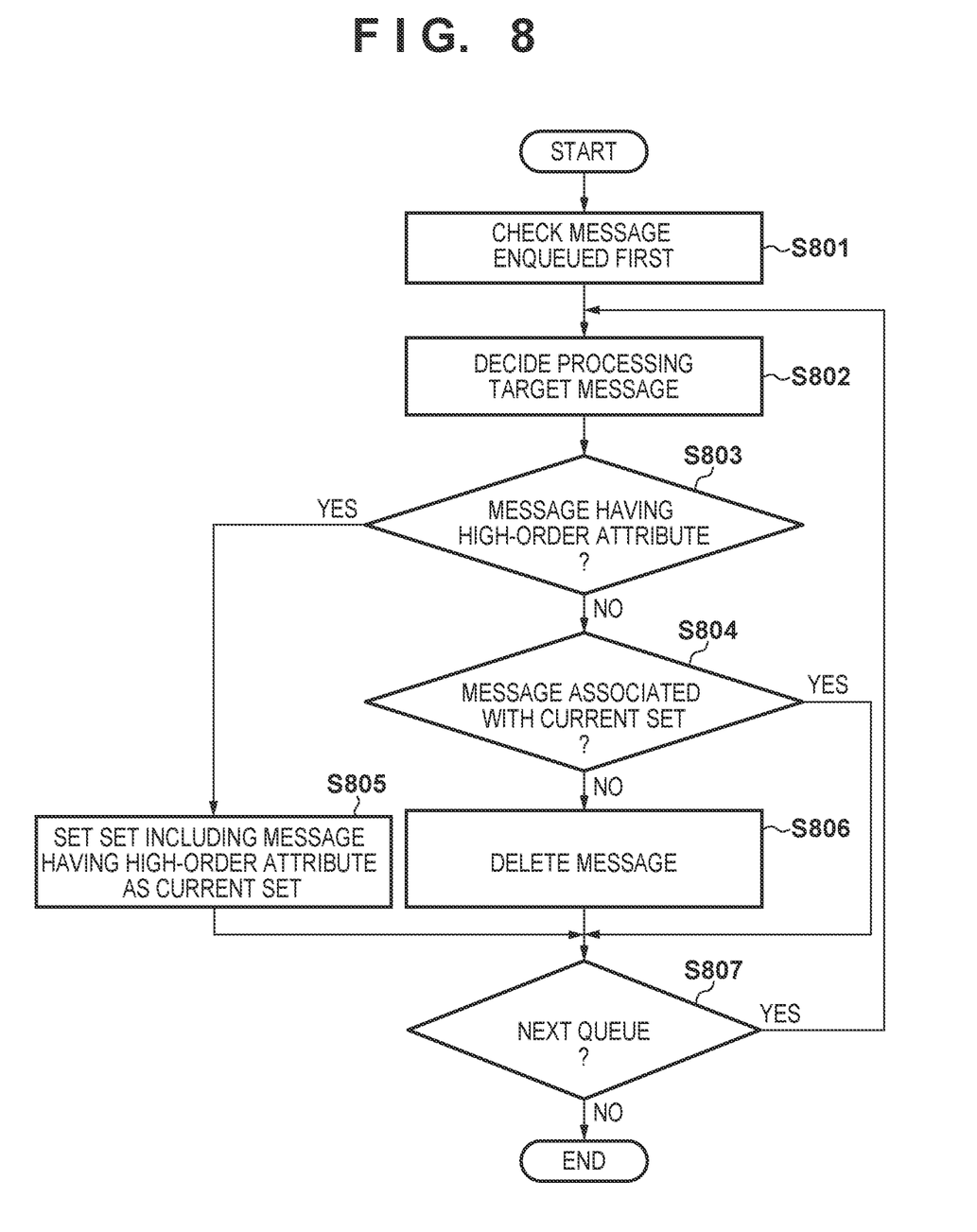
FIG. 8 is a flowchart for explaining processing in a communication control unit according to the second embodiment.

The second embodiment will be described next. Differences between the first and second embodiments will be described below. FIG. 8 is a flowchart for explaining a procedure of processing in the communication control unit 16 of the first control application 13. The first embodiment has exemplified the arrangement configured to check one of the messages held in the processing waiting queue 168 (queue holding unit) which is held (enqueued) in the processing waiting queue 168 first after the stoppage of dequeue processing and set the checked message as a processing target. The second embodiment will exemplify an arrangement configured to check the message held (enqueued) in a processing waiting queue 168 lastly after the stoppage of dequeue processing and set the checked message as a processing target.

In step S801, a deletion processing unit 167 checks the message, of the messages held in the processing waiting queue 168 (queue holding unit), which is held (enqueued) in the processing waiting queue 168 lastly after the stoppage of dequeue processing.

FIG. 6 shows an example of current information. A set 601 of all messages indicates an example of classifying messages according to screen transitions and screen states. The set 601 of all the messages includes subsets 61a, 62b, and 63. The subset 61a includes a message concerning the display state of a screen A 611 and messages concerning operations 612 to 615 on screen A. The subset 62b includes a message concerning the display state of a screen B 621 and messages concerning operations 622 to 625 on screen B. The subset 62b includes a message concerning the display state of a subscreen 625 of screen B and operations 626 and 627 on the subscreen of screen B. The subset 63 includes messages 631 to 633 concerning information notifications 1, 2, and 3 as messages each having a high-order attribute.

If, for example, the message held (enqueued) lastly in the processing waiting queue 168 is the message concerning the operation 612 on screen A, the current set (subset) of messages is the subset 61a having the display state of the screen A 611 as a high-order attribute.

In step S802, the deletion processing unit 167 decides a processing target message. In this embodiment, the deletion processing unit 167 sequentially decides processing target messages, starting from the message held (enqueued) lastly in the processing waiting queue 168 after the stoppage of dequeue processing. The message decided as the first processing target is the newest one of the messages held in the processing waiting queue 168. Subsequently, the messages are sequentially decided as processing targets from newest to oldest.

Processing in step S803 is the same as that in step S703. If the deletion processing unit 167 determines that the processing target is a message having a high-order attribute, the process advances to step S805.

In step S805, the deletion processing unit 167 sets a message subset having a high-order attribute as a current set as a processing target. That is, if the information notification (message) held in the processing waiting queue 168 lastly after determination of disconnection of communication is an information notification having a high-order attribute, the deletion processing unit 167 specifies an information notification set constituted by the information notification having the high-order attribute and information notifications (associated messages) associated with the information notification having the high-order attribute.

The deletion processing unit 167 saves the information of the current set in a temporary memory for processing. In the subsequent processing, the deletion processing unit 167 can perform determination based on the comparison result obtained by comparing information in step S804. If, for example, a message having a high-order attribute is a message concerning the display state of the screen A 611, the information of the current set includes the message concerning the display state of the screen A 611 and messages concerning the operations 612 to 615 on screen A. This information is saved as the information of the current set in the temporary memory.

Upon determining in step S803 that the processing target message is not a message having a high-order attribute, the deletion processing unit 167 advances the process to step S804.

In step S804, the deletion processing unit 167 determines whether the processing target message is an associated message of the current set (subset), that is, an associated message associated with a message having a high-order attribute (main message). If, for example, the main message indicates the display state of the screen A 611, the deletion processing unit 167 determines whether the processing target message is an associated message (a message concerning one of the operations 612 to 615 on screen A) subordinate to the main message. The deletion processing unit 167 compares the information of the current set with the information saved in the temporary memory. If the processing target message (current information) is not saved in the temporary memory, the deletion processing unit 167 determines that the processing target message is not an associated message of the current set (subset).

If the processing target message is an associated message of the current set (subset) (YES in step S804), the process advances to step S807. In contrast, if the deletion processing unit 167 determines in step S804 that the processing target message is not an associated message of the current set (subset) (NO in step S804), the process advances to step S806. In step S806, the deletion processing unit 167 performs deletion processing of any information notification that is not included in the information notification set (current set). That is, the deletion processing unit 167 deletes any message that is not an associated message of the current set (subset), and the process advances to step S807.

In step S807, the deletion processing unit 167 determines whether there is a next message held in the processing waiting queue 168. If the deletion processing unit 167 determines in step S807 that there is a next message (YES in step S807), the process returns to step S802 to repeat similar processing. In contrast, if the deletion processing unit 167 determines in step S807 that there is no next message in the processing waiting queue 168 (NO in step S807), this processing is terminated.

Third Embodiment

The third embodiment will be described next. The first embodiment has exemplified the arrangement including the connection monitoring unit provided on the first control application 13 side. However, the embodiment is not limited to this arrangement. For example, the connection monitoring unit can be provided on the second control application 14 side.

A second control application 14 includes a connection monitoring unit that monitors a connection state with the first control application. When the connection monitoring unit determines that the connection state is a disconnection state, the GUI provided by the second control application 14 can display, as "UserUnkown", information indicating that no subject information can be obtained or notification information indicating a non-connection state. For example, a control unit 142 can cause the GUI of a portable terminal 140 to perform display by performing display control of the GUI based on the monitoring result obtained by the connection monitoring unit on the second control application 14 side. Alternatively, it is possible to perform notification to stop communication concerning information (for example, a subset of messages corresponding to operations from the start of an examination to the end of the examination or a subset of messages corresponding to operations for one unit of imaging) communicated between the first and second control applications.

Fourth Embodiment

The fourth embodiment will be described next. This embodiment will exemplify an arrangement configured to set a priority for each message subset. A deletion processing unit 167 can assign information notification (message) sets with priorities for setting a preferential order of processing and change the order of information notifications based on the assigned priorities.

For example, it is possible to assign subsets 61a, 62b, and 63 included in a set 601 of all messages with priorities for setting a preferential order of processing. The deletion processing unit 167 can change the processing order of queues based on the priorities. For example, the deletion processing unit 167 can change the order so as to preferentially process message queues concerning patient information or, as in the subset 63, preferentially process independent notifications (messages 631 to 633 concerning information notifications 1, 2, and 3) having no associated message and respectively constituted by messages each having a high-order attribute.

According to each embodiment described above, in the system in which a plurality of applications execute processing in cooperation with each other, even when the connection between applications is disconnected first and then reconnected, it is possible to solve an information mismatch caused between the applications.

The present invention can solve disconnection problems in a network in a system in which two different applications simultaneously operate in cooperation with each other via a wireless or wired network, and even at the occurrence of disconnection, can notify information for restoring the states of the two applications to a latest state after reconnection. In addition, the present invention has the effect of improving responsiveness to improve the efficiency of restoration to the latest state.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-045137, filed Mar. 12, 2019, which is hereby incorporated by reference herein in its entirety.

What is claimed is:

1. A radiation imaging system that can control a radiation generating apparatus and a radiation detector based on communication between a first control application and a second control application, the system comprising:
   at least one memory storing instructions; and
   at least one processor that, when executing the instructions, causes the radiation imaging system to function as:
      a connection monitoring unit configured to monitor a connection state of the communication;
      a holding unit configured to hold an information notification indicating a control state of an imaging control unit of the first control application that performs the control in a case where the connection monitoring unit determines that the connection state is a disconnection state; and
      a deletion processing unit configured to perform deletion processing of the information notification held in the holding unit so as to leave an information notification indicating a final state of control by the imaging control unit,
   wherein the deletion processing unit specifies an information notification as a deletion target based on an attribute of the information notification,
   wherein in a case where the information notification held in the holding unit firstly after determination of the disconnection state is an information notification having a high-order attribute, the deletion processing unit specifies an information notification set constituted by including the information notification having the high-order attribute and an information notification associated with the information notification having the high-order attribute, and
   wherein the deletion processing unit performs deletion processing of an information notification belonging to the information notification set which is held in the holding unit before processing a target information notification.

2. The system according to claim 1, further comprising:
   a control unit configured to control obtaining of the information notification held in the holding unit based on a monitoring result obtained by the connection monitoring unit;
   an obtaining unit configured to obtain the information notification held in the holding unit; and
   a communication unit configured to transmit the information notification obtained by the obtaining unit to the second control application,
   wherein the control unit causes the obtaining unit to stop obtaining the information notification in a case where the connection monitoring unit determines the disconnection state.

3. The system according to claim 1, wherein when the information notification held in the holding unit lastly after determination of the disconnection state is the information notification having the high-order attribute, the deletion processing unit specifies an information notification set constituted by including the information notification having the high-order attribute and an information notification associated with the information notification having the high-order attribute.

4. The system according to claim 3, wherein the deletion processing unit performs deletion processing of an information notification that is not included in the specified information notification set.

5. The system according to claim 1, wherein the information notification includes a notification concerning a screen transition of a GUI provided by the first control application.

6. The system according to claim 5, wherein the information notification includes a notification concerning an in-screen operation of the GUI provided by the first control application.

7. The system according to claim 1, wherein the information notification includes a notification concerning a state of radiation imaging by the imaging control unit of the first control application.

8. The system according to claim 1, wherein the second control application comprises the connection monitoring unit configured to monitor the connection state of communication with the first control application, and
wherein a GUI provided by the second control application is caused to display that subject information cannot be obtained in a case where the connection monitoring unit determines that the connection state is the disconnection state.

9. The system according to claim 1, wherein the deletion processing unit assigns the information notification set with a priority for setting a preferential order of processing, and changes an information notification order based on the assigned priority.

10. The system according to claim 2, wherein the control unit causes the obtaining unit to resume obtaining the information notification in a case where the connection monitoring unit determines that reconnection is made after determining the disconnection state.

11. The system according to claim 10, wherein the communication unit obtains the information notification from the holding unit having undergone deletion processing by the deletion processing unit and transmits the information notification to the second control application.

12. A method of controlling a radiation imaging system that can control a radiation generating apparatus and a radiation detector based on communication between a first control application and a second control application, the method comprising:
monitoring a connection state of the communication;
holding an information notification indicating a control state of an imaging control unit of the first control application that performs the control in a case where it is determined in the monitoring that the connection state is a disconnection state; and
performing deletion processing of the information notification held in a holding unit so as to leave an information notification indicating a final state of control by the imaging control unit,
wherein an information notification is specified as a deletion target based on an attribute of the information notification,
wherein in a case where the information notification held in the holding unit firstly after determination of the disconnection state is an information notification having a high-order attribute, an information notification set is specified to be constituted by including the information notification having the high-order attribute and an information notification associated with the information notification having the high-order attribute, and
wherein the deletion processing of an information notification belonging to the information notification set which is held in the holding unit is performed before processing a target information notification.

13. The method according to claim 12, further comprising:
controlling obtaining of the information notification held in the holding unit based on a monitoring result obtained in the monitoring;
obtaining the information notification held in the holding unit; and
transmitting the information notification obtained in the obtaining to the second control application,
wherein in the controlling, obtaining of the information notification is stopped in the obtaining in a case where the disconnection state is determined in the monitoring.

14. The method according to claim 12, wherein the information notification includes a notification concerning a screen transition of a GUI provided by the first control application.

15. The method according to claim 12, wherein the information notification includes a notification concerning a state of radiation imaging by the imaging control unit of the first control application.

16. The method according to claim 12, wherein the second control application comprises causing a monitoring unit that monitors the connection state of communication with the first control application to monitor the connection state, and
wherein in a case where it is determined in the causing the monitoring unit that the connection state is the disconnection state, a GUI provided by the second control application is caused to display that no subject information can be obtained.

17. The method according to claim 12, wherein in the performing deletion processing, the information notification set is assigned with a priority for setting a preferential order of processing, and an information notification order is changed based on the assigned priority.

* * * * *